United States Patent [19]

Austin et al.

[11] 4,238,417
[45] Dec. 9, 1980

[54] DECOMPOSITION OF CUMENE HYDROPEROXIDE AND RECOVERY OF BORON TRIFLUORIDE CATALYST

[75] Inventors: Richard G. Austin, Churchill Borough; Wayne R. Pretzer; Thaddeus P. Kobylinski, both of Gibsonia, all of Pa.

[73] Assignee: Gulf Research & Development Company, Pittsburgh, Pa.

[21] Appl. No.: 66,520

[22] Filed: Aug. 15, 1979

[51] Int. Cl.³ ............................................. C07C 45/53
[52] U.S. Cl. .............................. 568/385; 568/754; 423/293
[58] Field of Search ................... 260/593 A; 568/768, 568/754; 423/293

[56] References Cited

U.S. PATENT DOCUMENTS

| | | |
|---|---|---|
| 2,718,530 | 9/1955 | Cowner ........................ 260/593 A X |
| 2,728,796 | 12/1955 | Vandenberg ................. 260/593 A X |
| 2,776,320 | 1/1957 | Thompson .................... 260/593 A X |
| 3,376,352 | 4/1968 | Domenicali et al. ................. 568/768 |
| 4,006,194 | 2/1977 | Luberoff et al. ............ 260/593 A X |

FOREIGN PATENT DOCUMENTS

| | | | |
|---|---|---|---|
| 805048 | 11/1958 | United Kingdom ...................... 568/754 |
| 1412308 | 11/1975 | United Kingdom ...................... 568/754 |

*Primary Examiner*—Bernard Helfin

[57] ABSTRACT

Cumene hydroperoxide is decomposed to phenol and acetone using boron trifluoride or a boron trifluoride complex as the decomposition catalyst. The boron trifluoride in the reaction product is reacted with a phosphorus-containing salt of an alkali metal such as sodium phosphate for recovery and reuse in the process.

13 Claims, No Drawings

DECOMPOSITION OF CUMENE HYDROPEROXIDE AND RECOVERY OF BORON TRIFLUORIDE CATALYST

FIELD OF THE INVENTION

This invention relates to the catalytic cleavage of cumene hydroperoxide to equal molar portions of phenol and acetone using boron trifluoride as the catalyst, and more particularly it relates to a process for the catalytic cleavage of cumene hydroperoxide in the presence of boron trifluoride or a complex of boron trifluoride with an oxygen-containing polar compound in which the boron trifluoride in the product is deactivated by reaction with a phosphorus-containing salt of an alkali metal. The boron trifluoride is subsequently recovered from the complex formed with this phosphorus-containing salt such as sodium phosphate and is recycled to the process.

DESCRIPTION OF THE PRIOR ART

Cumene can be readily oxidized with air to form cumene hydroperoxide and the hydroperoxide can then be decomposed to form equal molar amounts of phenol and acetone. In the commercial process for producing phenol by this general method, a small amount of a mineral acid, generally sulfuric acid, is used as the decomposition or cleavage catalyst. Since phenol and acetone are the products of the cleavage reaction, the reaction solvent can conveniently be a phenol-acetone solution. In this process the cumene hydroperoxide instantaneously decomposes to phenol and acetone as it is slowly added in solution with cumene to the mineral acid solution. The highly exothermic reaction is controlled by the rate of cumene hydroperoxide addition and by acetone reflux. Water is substantially excluded from the reaction medium during the decomposition reaction to insure homogeneity. Since the mineral acid is neutralized in the product stream with an alkali solution to reduce tar formation during subsequent distillative separation of the phenol and acetone from the tars, the resulting alkali sulfate sludge by-product must be disposed of and new acid must be continuously supplied to the process.

DESCRIPTION OF THE INVENTION

The desired decomposition of cumene hydroperoxide is a cleavage to equal mols of phenol and acetone, that is, about 62 weight percent phenol and 38 weight percent acetone. In using sulfuric acid as the decomposition catalyst, a selectivity to phenol of about 85 to 95 percent is generally obtained. The non-selective decomposition product particularly as catalyzed by a strong mineral acid includes cumyl alcohol, acetophenone, methylbenzofuran, several organic acids, mono- and dicumylphenol, diacetone alcohol, acetol, mesityl oxide, phorone, alpha-methylstyrene and various oligomers of alpha-methylstyrene which are tar-like substances. When the reaction product is distilled, these by-products remain in the residue which is collectively called "tar" or "tars". It has been reported that the main products in this "tar" are cumylphenol and dicumylphenol, the polymers of alpha-methylstyrene, acetophenone and diacetone alcohol. Since few of these by-products of the non-selective reaction can be economically recovered, this non-selective reaction represents a significant economic loss.

A particular advantage in the use of the boron trifluoride and complexed boron trifluoride decomposition catalysts is that a selectivity greater than 95 percent, approaching 100 percent under optimum conditions, can be obtained. Another advantage of these catalysts in contrast with the strong mineral acid catalyst is that the boron trifluoride catalysts do not promote the alkylation of phenol product to cumylphenol nor the oligomerization of aromatic olefin to form tars. Furthermore, in the present process the major by-product, if any, alpha-methylstyrene, can be recovered and hydrogenated to cumene for recycle in the process. A further advantage in the use of the boron trifluoride catalysts instead of the mineral acid catalysts is that the corrosion problems of the latter are substantially avoided.

The mineral acid in the crude decomposition product resulting from the mineral acid catalyzed cleavage reaction is deactivated by neutralization with a suitable basic substance prior to distillation of the crude mixture for the separation of the phenol and acetone product from the tar, otherwise the mineral acid will catalyze substantial additional tar formation during distillation. Thus, we have determined that distillation of a portion of a sulfuric acid catalyzed decomposition product resulted in 12 percent tar while only 4.4 percent tar resulted overall in another portion of the same decomposition product which was distilled after neutralization with sodium bicarbonate. But this neutralization procedure, which includes downstream caustic and acid washes, introduces water into the reaction product. This requires additional distillation equipment for water removal and requires additional treatment of the separated water for phenol removal prior to its disposal. A separator is also required for the removal of precipitated sodium sulfate. A substantial economic burden is superimposed onto the mineral acid-catalyzed decomposition process including capital, labor and energy costs as a result of the catalyst neutralization and associated procedures.

In contrast, in the present procedure, the catalyst is deactivated for product distillation in a non-aqueous procedure by reacting the boron trifluoride catalyst with a phosphorus-containing salt to form a stable coordination compound. This coordination compound will not decompose at the temperatures required to distill off the products and by-products from the product solution but it can be decomposed at higher temperatures. As a result, neutralization and water removal problems are eliminated from the system and product separation is greatly simplified. And most advantageously the complex of the boron trifluoride and the phosphorus-containing salt can be decomposed after product separation, to release both the phosphorus-containing salt and the boron trifluoride for separate recovery and recycle in the process. This recovery of boron trifluoride not only provides an economic saving, but it also substantially reduces environmental problems which would result from discharging it as a waste.

The phosphorus-containing salts which we find to be suitable for complexing with the boron trifluoride are the alkali metal phosphates and alkali metal pyrophosphates. Of particular suitability are sodium phosphate, $Na_3PO_4$; sodium pyrophosphate, $Na_4P_2O_7$; potassium phosphate, $K_3PO_4$ and potassium pyrophosphate, $K_4P_2O_7$. The primary function of this phosphorus-containing salt is to produce a sufficiently strong complex with the boron trifluoride to retain the boron trifluoride in the residue resulting from the product distillation notwithstanding rigorous distillation conditions.

When boron trifluoride gas is used as the catalyst, it can be bubbled into the reaction liquid or the desired quantity can be added to the free space in the reactor from which it will readily dissolve in the reaction liquid. We have found that catalyst concentration is an important reaction variable. That is, the higher the catalyst concentration, the more rapid the reaction until too much catalyst renders the exothermic reaction uncontrollable. On the other hand, the reaction is too slow with too little catalyst. Within these constraints the concentration of non-complexed boron trifluoride catalyst will generally be between about 20 parts of boron trifluoride per million parts of total reaction liquid (ppm.), and about one percent, or even higher with appropriate control of reaction temperature and preferably its concentration will be between about 500 ppm. and about 0.5 percent.

The complexed boron trifluoride catalyst is a liquid or solid which is readily dissolved in the reaction liquid. Suitable complexes can be formed with boron trifluoride and water or an appropriate oxygen-containing organic polar compound in which oxygen acts as the electron donor. These organic polar compounds include aliphatic alcohols having one to about four carbon atoms; aromatic alcohols such as benzyl alcohol; aliphatic ethers having from two to about eight carbon atoms; or mixed alkyl-aromatic ethers such as methylphenyl ether; aliphatic acids having from one to about four carbon atoms or aromatic acids such as phenol and benzoic acid; acid anhydrides such as acetic acid anhydride; esters formed from aliphatic acids having from one to about four carbon atoms esterified with an alkyl group containing one to about four carbon atoms or with an aromatic group such as phenyl and benzyl; an aliphatic ketone having from two to about eight carbon atoms, an aromatic ketone such as dibenzyl ketone or a mixed alkyl-aromatic ketone; aliphatic aldehydes having from two to about four carbon atoms or an aromatic aldehyde such as benzyl aldehyde; and the like. Also useful as a complexing agent for the boron trifluoride are suitable chlorine derivatives of the above such as chloroethyl alcohol, dichloroethyl alcohol, trichloroacetaldehyde, and the like. Free boron trifluoride, which is dissolved in the reaction liquid, readily complexes with phenol which is produced as the reaction proceeds. Nevertheless, we have found that the reaction proceeds more rapidly when free boron trifluoride is used as the catalyst than when this boron trifluoride complex with phenol is initially used as the catalyst since the free boron trifluoride is a much more active catalyst.

The boron trifluoride complex can be either a 1:1 or a 2:1 molar complex of the complexing agent with the boron trifluoride provided that the complex can be produced and is stable at the conditions of the decomposition reaction. The concentration of the boron trifluoride in the reaction liquid depends, in part, on the properties of the complex. For example, some complexes are active at very low concentrations, while other complexes require substantially higher amounts for a suitable rate of reaction. The more active complexes of boron trifluoride, such as the 1:1 complex with diethyl ether, are similar in activity to free boron trifluoride. The concentration range for free boron trifluoride in the reaction liquid, as specified above, also applies to the complexes of boron trifluoride.

Since the cleavage reaction is highly exothermic, temperature control of the reaction liquid is generally provided. This temperature control can be accomplished by controlling the amount of catalyst used or by controlling the rate at which the catalyst is mixed with the cumene hydroperoxide. But with the highly active catalysts one or both of the following techniques for temperature control is desirably utilized. Temperature control can be effected, in part, by maintaining appropriate means for the positive cooling of the reaction liquid during the reaction such as by solvent reflux or by submerged cooling coils. Another effective and useful method of temperature control is the employment of sufficient inert solvent to serve as a heat sink. The reaction can be carried out within the range of between about 25° to about 110° C. and preferably a range of between about 60° to about 80° C. At the lower temperatures the reaction becomes quite slow although highly selective, while undesirable tar formation can result at higher temperatures due to the effects of thermal decomposition of the cumene hydroperoxide.

The pressure within the reactor is not a critical factor during the decomposition reaction. Generally, the pressure will range from a pressure moderately below to moderately above atmospheric pressure. Since boron trifluoride gas is highly soluble in the reaction liquid, the boron trifluoride gas pressure need only be moderately elevated above atmospheric pressure to obtain its solution in the liquid reaction medium.

The cumene hydroperoxide can desirably be prepared by oxidation of cumene with air in the conventional manner. In this process a solution of at least about 10 weight percent cumene hydroperoxide in cumene is desirably produced, although a product containing less than 10 weight percent cumene hydroperoxide can be utilized. Since it is not particularly desirable to use an excessive amount of cumene in a continuous process as a reaction solvent due to subsequent handling and separation problems, it is preferred that a more concentrated solution of cumene hydroperoxide be prepared. In this oxidation reaction the maximum concentration of cumene hydroperoxide that can conveniently be produced is about 30 percent.

The cumene hydroperoxide to be used in the decomposition reaction can be further concentrated by flashing off sufficient cumene to form a feed solution of between about 60 to about 90 percent, preferably about 65 to about 80 percent, cumene hydroperoxide. Although pure cumene hydroperoxide can be used, it is not desirable to obtain it in this final stage of purity for economic reasons and also for safety reasons since the presence of some cumene tends to stabilize the cumene hydroperoxide. The decomposition reaction can suitably be carried out with as little as about 0.1 weight percent cumene hydroperoxide in the reaction liquid, with at least about 0.5 percent being preferred and at least about 1.0 percent being most preferred. The maximum amount of cumene hydroperoxide in the cleavage reaction liquid will suitably be about 20 weight percent, preferably about 10 percent and most preferably about 5 percent. Since explosions have in the past resulted from cumene hydroperoxide reactions which have run away, it is generally desired to carry out the reaction with substantial diluent as a safety measure, resulting in a concentration of cumene hydroperoxide in the reaction liquid much below the upper limit.

The solvent used in this process can be the cumene associated with the cumene hydroperoxide as described above. However, since phenol and acetone are the desired reaction product, a phenol-acetone solvent is generally desirable in order to simplify product separation. Since a solution of cumene hydroperoxide and cumene is usually added to the reactor, the solvent system will therefore include cumene as a component, generally a minor component. The solvent can conveniently be the 1:1 molar phenol to acetone product of the cumene hydroperoxide cleavage reaction, however, variations in the relative proportions can be used. Thus, although there is no particular advantage to using an excess of phenol, an excess of acetone may be desirable, particularly if the acetone is to be utilized for temperature maintenance during reaction by means of acetone reflux or boil-off. Therefore, the mol ratio of acetone to phenol as the solvent in the reaction mixture can be as high as about 10:1 and preferably no higher than about 3:1. Other usable solvents include aromatic solvents such as benzene, toluene, and the like; ethers such as diethyl ether and tetrahydrofuran, or any other solvent which is compatible with the reactant and catalyst and can be conveniently separated.

Phenol is not inert when used as a solvent for cumene hydroperoxide in its decomposition. Rather phenol, by virtue of its acid nature, has been found to be a catalyst for the decomposition of cumene hydroperoxide in a reaction which is significantly slower than the above-described mineral acid catalyzed reaction. Moreover, the selectivity of this phenol catalyzed decomposition of cumene hydroperoxide is very poor, being less than 80 percent selectivity to phenol as determined by a study of the reaction. It is readily apparent that the presence of solvent phenol in the mineral acid catalyzed reaction of the commercial processes is not noticeably detrimental because the great speed of the mineral acid catalyzed decomposition effectively eliminates the detrimental effect on selectivity of the relatively slow phenol catalyzed reaction. In our reaction we can avoid a significant adverse effect on product selectivity from the phenol catalyzed reaction, particularly when phenol is present as an added solvent, by appropriate catalyst selection and/or concentration to obtain a suitably rapid reaction.

When operating under the general conditions described herein, particularly within a temperature range between about 60° and 80° C., the decomposition reaction to substantial completion, as a batch or as a continuous process, will take place in about two minutes to about two hours, and preferably will take place in about five to about 45 minutes. The process can also be carried out in a semi-continuous manner in which the reactant, solvent and catalyst are continuously added to a stirred tank reactor at a rate coinciding with the withdrawal rate, sufficient to provide a suitable average reaction rate within the above time ranges for substantially complete reaction. Since a significant quantity of unreacted cumene hydroperoxide in the final reaction product can undesirably interfere with the distillative separation procedure, it is preferred that there be a substantially complete decomposition of the cumene hydroperoxide in the reaction stage.

After the cumene hydroperoxide decomposition reaction is completed, the product solution is treated with the alkali metal phosphate or pyrophosphate in order to bind the boron trifluoride with this salt in a stable coordination compound. If the catalyst is boron trifluoride itself, the phosphorus-containing salt directly reacts with the boron trifluoride to form the complex. If the catalyst is a coordination compound of boron trifluoride and the oxygen-containing polar compound, the phosphorus-containing salt will react with this catalyst complex displacing and freeing the oxygen-containing polar compound. The phosphate or pyrophosphate salt is able to displace the oxygen-containing polar compound from its complex with the boron trifluoride because the complex of this salt with boron trifluoride is the stronger and more stable complex.

The phosphate salt can complex with from one to three mols of boron trifluoride while the pyrophosphate salt can complex with from one to four mols of the same. At least about a stoichiometric amount of the salt should be added to tie up the boron trifluoride, that is, at least about 0.25 mol of the phosphate salt and at least about 0.33 mol of the pyrophosphate salt per mol of boron trifluoride in the product solution. To insure that all of the boron trifluoride is complexed so that there is no carry-over of it into the distillate it is preferred that an excess of either salt be used, that is, at least about 0.4 mol of the phosphate or pyrophosphate salt be used per mol of boron trifluoride up to a molar ratio of 1:1 or higher, such as 5:1, but such excess amounts may be of no particular advantage.

The product solution is then distilled under appropriate conditions of temperature and pressure to drive off the volatile components in the solution including acetophenone without dissociating the complex of boron trifluoride with the phosphorus-containing salt. Under these conditions of operation the only materials remaining in the still are the complex and the polymeric tar solids. The temperature in the still is then elevated to the decomposition temperature of the complex, or higher, to dissociate the complex and volatilize the boron trifluoride for separate recovery. The phosphate or pyrophosphate salt is recovered from the residue by dissolving the salt in water.

It may be desirable in certain instances to distill off the volatile compounds in the reaction product, including acetophenone, at a reduced pressure and temperature to improve the separation of the acetophenone and minimize formation of tars during distillation. For these reasons this distillation can be carried out at a temperature as low as about 150° C. and a pressure of about one millimeter of mercury, but it is preferred to use distillation conditions of at least about 160° C. and a pressure of at least about 30 mm Hg. and most preferably a distillation temperature of at least about 200° C. is used. If distillation is carried out at about atmospheric pressure (760 mm. Hg.), the temperature must be at least as high as the boiling point of acetophenone (201.7° C.). A pressure higher than atmospheric pressure can be used in the distillation but there is no advantage to using such elevated pressures. The distillation can be effected at a temperature up to about the decomposition temperature of the coordination compound, but preferably distillation conditions should be maintained substantially below this temperature to avoid any dissociation of this complex and carry-over of boron trifluoride into the distillate.

After this distillation is completed, the residue containing the coordination compound and the polymeric tar solids is further heated to dissociate the boron trifluoride from the phosphate or pyrophosphate salt for separate recovery of these two components. This decomposition can be accomplished by heating the residue to the decomposition temperature of the particular complex, but preferably higher and condensing out the volatilized boron trifluoride in a cold trap. If this decomposition temperature is sufficiently high as to cause a partial decomposition and distillation of the polymeric tar solids, then it is necessary to separate out and recover the boron trifluoride from the distillation vapors.

DESCRIPTION OF PREFERRED EMBODIMENTS

In the following examples, the hydroperoxide was analyzed by iodometric titration with sodium thiosulfate. The boron analysis was carried out by converting the boron to a water soluble acid or salt and then quantitatively measuring it by atomic absorption. The decomposition product resulting from the boron trifluoride, both free and complexed, catalyzed reactions was light yellow in color and transparent, indicating very slight tar, while the sulfuric acid catalyzed product liquid was black and opaque. Both the residue and the product distillate were analyzed. Many of the analyses in the following examples add up to 100 percent due to product averaging becuse the actual "tar" value was less than one percent as indicated where specific tar analyses were made. The analyses for compounds other than hydroperoxide and boron were accomplished by gas chromatography or by high performance liquid chromatography.

EXAMPLE 1

The catalytic activity of sulfuric acid for the decomposition of cumene hydroperoxide was observed. A 57.3 percent solution of cumene hydroperoxide in cumene was added dropwise into 100 ml. of a two percent solution of sulfuric acid in acetone in a 300 ml. round bottom flask open to the atmosphere. Each drop instantly decomposed as it contacted the solution. Since no positive cooling of the reaction liquid was provided, the temperature of the solution rose from room temperature (about 25° C.) at the beginning of the addition to 44° C. upon the completion of the addition. A total of 35.2 g. of the cumene hydroperoxide was added over 60 minutes. Analysis of the product showed that 99.9 percent of the cumene hydroperoxide had reacted at a selectivity of 93 percent to phenol.

EXAMPLE 2

The following reactions were carried out in a glass reactor equipped with a magnetic stirrer and operated at a pressure within the reactor slightly above atmospheric pressure. The reactor was cooled by a cold finger in the liquid. Small samples of the reaction liquid (about 1 ml.) were periodically withdrawn to monitor the reaction.

Phenol was tested as a decomposition catalyst for cumene hydroperoxide at several temperatures. About 20 g. of a solution consisting of 5 parts phenol, 3 parts acetone and 1 part cumene were placed in the reactor. About 2 ml. of a solution consisting of 55 percent cumene hydroperoxide in cumene were injected into the reactor in each experiment. Table I summarizes the results of these experiments.

TABLE I

| | Cumene Hydroperoxide Decomposed, % | | | |
|---|---|---|---|---|
| | Minutes | | | |
| Temp. | 10 | 20 | 50 | 100 |
| 40° C. | trace | trace | trace | trace |
| 60° C. | — | 8 | 19 | 39 |

TABLE I-continued

| | Cumene Hydroperoxide Decomposed, % | | | |
|---|---|---|---|---|
| | Minutes | | | |
| Temp. | 10 | 20 | 50 | 100 |
| 80° C. | 18 | 34 | 60 | 85 |

The experiment at 80° C. was allowed to run for four and one-half hours at which time the cumene hydroperoxide was completely decomposed. Analysis of this product mixture disclosed that it contained 77 percent phenol, 8 percent alpha-methylstyrene, 4 percent acetophenone, 4 percent dimethylbenzyl alcohol, and 7 percent of a residuum consisting of aromatic carbonyls, aromatic alcohols, substituted phenols, substituted benzofurans and methylstyrene oligomers.

EXAMPLES 3–5

A 200 ml. glass reactor partially immersed in a heated oil bath at 60° C. and equipped with a magnetic stirrer and a cold finger was used in these experiments. The cold finger was cooled with tap water and was only used when necessary to prevent excessive temperatures. A series of three experiments was carried out using different amounts of boron trifluoride gas as the catalyst. The reactor was charged with 22 g. of a 20 percent solution of cumene hydroperoxide (CHP) which heated to 60° C. Boron trifluoride gas in a predetermined amount was bubbled into the liquid to initiate the decomposition reaction. One ml. samples were taken at intervals to monitor completion of the reaction. The results of these experiments, after greater than 99 percent decomposition of the cumene hydroperoxide, are set out in Table II.

TABLE II

| Example | 3 | 4 | 5 |
|---|---|---|---|
| CHP solution, g. | 22 | 22 | 22 |
| BF₃ conc., ppm. | 340 | 136 | 27 |
| Time, min. | <5 | 30 | 60 |
| Final Temp, ° C. | 100 | 72 | 64 |
| Selectivity | | | |
| phenol | 92 | 90 | 98 |
| alpha-methylstyrene | 3 | 4 | 1 |
| acetophenone | 3 | 4 | 1 |
| dimethylbenzyl alcohol | 2 | 2 | — |

EXAMPLES 6–8

A second series of three experiments was conducted using the same reactor and 22 g. of a 20 percent solution of cumene hydroperoxide. In these experiments different amounts of a solution of the 1:1 complex of boron trifluoride with diethyl ether in acetone, at a concentration of one ml. per liter of acetone, were added, after the cumene hydroperoxide solution had reached 60° C., to initiate the decomposition reaction. One ml. samples were taken at intervals to monitor the reaction. The results of these experiments are set out in Table III.

TABLE III

| Example | 6 | 7 | 8 |
|---|---|---|---|
| CHP solution, g. | 22 | 22 | 22 |
| BF₃ . O(Et)₂, conc., ppm. | 200 | 100 | 50 |
| Time, min. | <3 | 5 | 8 |
| Final temp., ° C. | 85 | 82 | 80 |
| CHP decomp., % | 99 | 99 | 99 |
| Selectivity | | | |
| phenol | 97 | 98 | 98 |
| alpha-methylstyrene | 2 | 1 | 1 |

TABLE III-continued

| Example | 6 | 7 | 8 |
|---|---|---|---|
| acetophenone | 1 | 1 | 1 |

EXAMPLE 9

A charge of 22 g. of the 20 percent solution of cumene hydroperoxide was placed in the reactor. After the solution had reached 60° C., one ml. of a solution of the 1:1 complex of boron trifluoride with isopropanol in acetone, at a concentration of 14 ml. per liter of acetone, was added to provide a concentration of 400 ppm. of the catalyst in the reactor. Complete decomposition of the cumene hydroperoxide occurred in about thirty minutes at a final temperature of 69° C. Analysis of the product disclosed a selectivity to phenol of 97 percent, to alpha-methylstyrene of 1.8 percent, to acetophenone of 0.7 percent and to dimethylbenzyl alcohol of 0.5 percent.

EXAMPLE 10

Another 22 g. charge of the 20 percent cumene hydroperoxide solution was placed in the reactor. After the solution had been warmed to 60° C., a sufficient quantity of a solution of the 1:2 complex of boron trifluoride with methanol in acetone, at a concentration of two ml. per liter of acetone, was added to provide a concentration of 104 ppm. of the boron trifluoride dimethanol complex in the reactor. Complete decomposition of the hydroperoxide was obtained in 45 minutes at a final temperature of 74° C. The selectivity to phenol was 97.5 percent, to alpha-methylstyrene two percent and to acetophenone 0.5 percent.

EXAMPLE 11

After a 22 g. charge of 20 percent cumene hydroperoxide had heated to 60° C., a 1:1 complex of boron trifluoride and phenol was introduced in sufficient amount to provide 435 ppm. of the catalyst complex. A maximum temperature of 67° C. was reached and complete decomposition occurred in 60 minutes at a selectivity of 97 percent to phenol, two percent to alpha-methylstyrene and one percent to acetophenone.

EXAMPLE 12

A 20 g. charge of a solution consisting of phenol, acetone and cumene in the weight ratio of 5:3:1, respectively, was placed in the reactor. After adding 1.83 g. of concentrated (80-82 percent) cumene hydroperoxide to the solution, it warmed to 60° C. One ml. of a solution of the 1:1 complex of boron trifluoride with diethyl ether in acetone, at a concentration of two ml. of the complex per liter of acetone was added to provide a concentration of the complex of 90 ppm. based on the total solution. Complete decomposition of the cumene hydroperoxide occurred in ten minutes.

EXAMPLE 13

A continuous flow reaction was carried out in a one liter flask equipped with a reflux column and a magnetic stirrer. About 300 ml. of acetone were added to the flask and warmed to 60° C. The catalyst, a solution of boron trifluoride monodiethyletherate complex in acetone, was pumped into the flask at a rate of about 350 ml. per hour, which provided a 0.3 percent concentration of the complex in the reaction liquid. Concentrated (80-82 percent cumene hydroperoxide in cumene was added at a rate of 750 ml. per hour. Product was continuously removed at a rate to maintain the liquid volume constant. Acetone was continuously distilled off and returned to the flask by reflux to maintain a flask temperature between 60° and 70° C. By analysis of the product stream, there was found to have been better than 99 percent conversion at a selectivity of about 98 percent to phenol, about two percent to alpha-methylstyrene and about one percent to acetophenone.

EXAMPLE 14

A solution containing 0.16 g. of the 1:1 complex of boron trifluoride and diethylether was heated to 60° C. and 20.46 g. of 80 percent cumene hydroperoxide was added slowly to control the temperature. After completion of the reaction, the solution was distilled at about 100 mm. Hg. pressure at a temperature ranging from 45° to 160° C. The distillate and tar were analyzed for boron. The analysis showed that there was 18.1 mg. of tar in the crude solution prior to the distillation and 14.3 mg. in the distillate and 4.3 mg., i.e. 23.8 percent, in the tar after distillation.

EXAMPLE 15

A 20 percent solution of cumene hydroperoxide in cumene was slowly added to 19.46 grams of an acetone solution of the 1:1 complex of boron trifluoride with diethylether containing 11.87 mg. of boron, maintained at about 60° C. with constant reflux, until 26.0 grams of the hydroperoxide solution was added. After the cumene hydroperoxide was completely decomposed, it was analyzed for boron and was found to contain 11.63 mg. of boron. A 2.0 gram quantity of sodium pyrophosphate was added to this product solution. The volatiles were distilled off at a maximum temperature of 160° C. and 100 mm. Hg. An analysis of the tar residue in the still found 11.37 mg. of boron in this residue, which was 95.3 percent of the boron introduced into the reactor. Upon raising the still pot temperature to about 400° C., the resulting boron trifluoride vapors condense out in a −196° C. trap.

EXAMPLE 16

An 80 percent solution of cumene hydroperoxide in cumene is slowly added to 0.16 gram of the 1:1 complex of boron trifluoride with diethylether in 14.0 grams of acetone at about 60° C. until 20.0 grams of the concentrated hydroperoxide solution have been added. After complete decomposition, the product solution is treated with 4.5 grams of sodium phosphate and heated for about 30 minutes at 50° C. to insure that the boron trifluoride complexes with the phosphate salt. The mixture is distilled at a temperature of about 160° C. and a pressure of about 100 mm. Hg. After the acetone, the phenol and the distillable by-products including acetophenone have been taken overhead, the residue containing the polymeric tars and the boron trifluoride complex is heated to about 400° C. The volatilized boron trifluoride is condensed in a trap cooled to −196° C. The tar is washed with water and the sodium phosphate is recovered from the water for reuse.

It is possible by appropriate correlation and control of the various variables involved in this process to minimize tar formation and optimize boron trifluoride recovery during the cumene hydroperoxide decomposition and the product separation stages.

It is to be understood that the above disclosure is by way of example and that numerous modifications and variations are available to those of ordinary skill in the art without departing from the true spirit and scope of the invention.

We claim:

1. The method for cleaving cumene hydroperoxide at high selectivity to phenol and acetone which comprises the steps
   (a) contacting a solution comprising about 0.1 to about 20 weight percent cumene hydroperoxide with a catalytic amount of boron trifluoride, a boron trifluoride complex with water or a boron trifluoride complex with an oxygen-containing polar organic compound at a temperature between about 25° and about 110° C. until the cleavage of said cumene hydroperoxide is substantially completed,
   (b) deactivating said catalyst by adding at least a stoichiometric amount of an alkali metal phosphate or alkali metal pyrophosphate whereby a coordination compound of said boron trifluoride and said alkali metal phosphate or alkali metal pyrophosphate is formed,
   (c) distilling the product solution at a temperature and a pressure whereby all components of the product solution are substantially distilled over except the said coordination compound of boron trifluoride with the said alkali metal phosphate or pyrophosphate and the polymeric tar solids formed during the cleavage reaction or during said distillation,
   (d) heating the residue to at least the decomposition temperature of the said coordination compound of boron trifluoride with the said alkali metal phosphate or pyrophosphate to dissociate said coordination compound and volatilize the boron trifluoride and
   (e) recovering said dissociated boron trifluoride.

2. The method for cleaving cumene hydroperoxide at high selectivity to phenol and acetone in accordance with claim 1 in which the catalyst is a complex of boron trifluoride with water, a dialkyl ether having between two and about eight carbon atoms or an alkyl alcohol having between one and about four carbon atoms and the catalyst is present in an amount between about 20 ppm. and about one weight percent.

3. The method for cleaving cumene hydroperoxide at high selectivity to phenol and acetone in accordance with claim 1 in which the solution comprises phenol and acetone in a mol ratio between about 1:1 and about 1.10 and between about one and about five weight percent cumene hydroperoxide.

4. The method for cleaving cumene hydroperoxide at high selectivity to phenol and acetone in accordance with claim 1 in which there is between about 500 ppm. and about 0.5 weight percent of the catalyst.

5. The method for cleaving cumene hydroperoxide at high selectivity to phenol and acetone in accordance with claim 1 in which the alkali metal is sodium or potassium and the dissociated alkali metal phosphate or pyrophosphate is removed from the said polymeric tar solids by dissolving the said salt in water.

6. The method for cleaving cumene hydroperoxide at high selectivity to phenol and acetone in accordance with claim 5 in which said distillation is carried out at a temperature of at least about 150° C. up to about the decomposition temperature of said coordination compound of boron trifluoride with said sodium or potassium salt.

7. The method for cleaving cumene hydroperoxide at high selectivity to phenol and acetone in accordance with claim 6 in which the distillation is carried out at a pressure between about 1.0 mm. Hg. and about atmospheric pressure.

8. The method for cleaving cumene hydroperoxide at high selectivity to phenol and acetone in accordance with claim 7 in which the distillation is carried out at a temperature of at least about 160° C. and a pressure of at least about 30 mm. Hg.

9. The method for cleaving cumene hydroperoxide at high selectivity to phenol and acetone in accordance with claim 6 in which the distillation is carried out at a temperature substantially below the said decomposition temperature.

10. The method for cleaving cumene hydroperoxide at high selectivity to phenol and acetone in accordance with claim 5 in which at least about a stoichiometric amount of said phosphate salt is added to form a 1:3 molar coordination compound with the boron trifluoride or at least about a stoichiometric amount of said pyrophosphate salt is added to form a 1:4 molar coordination compound with the boron trifluoride.

11. The method for cleaving cumene hydroperoxide at high selectivity to phenol and acetone in accordance with claim 10 in which a substantial molar excess of the said phosphate or pyrophosphate salt is added over the minimum amount required to complex with all of the boron trifluoride.

12. The method for cleaving cumene hydroperoxide at high selectivity to phenol and acetone in accordance with claim 5 in which the molar ratio of the phosphate or pyrophosphate salt and the boron trifluoride is at least about 1:1.

13. The method for cleaving cumene hydroperoxide at high selectivity to phenol and acetone in accordance with claim 5 in which the molar ratio of the phosphate or pyrophosphate salt and the boron trifluoride is between about 0.4:1 and about 5:1.

* * * * *

UNITED STATES PATENT OFFICE
CERTIFICATE OF CORRECTION

Patent No. 4,238,417  Dated December 9, 1980

Inventor(s) Richard G. Austin, Wayne R. Pretzer and Thaddeus P. Kobylinski

It is certified that error appears in the above-identified patent and that said Letters Patent are hereby corrected as shown below:

Col. 7, line 22, "becuse" should read --because--.

Col. 11, line 51 (claim 3), "1.10" should read --1:10--.

Signed and Sealed this

Twelfth Day of May 1981

[SEAL]

Attest:

RENE D. TEGTMEYER

Attesting Officer  Acting Commissioner of Patents and Trademarks